US011526987B2

(12) United States Patent
Tanabe et al.

(10) Patent No.: US 11,526,987 B2
(45) Date of Patent: Dec. 13, 2022

(54) IMAGE PROCESSING METHOD, PROGRAM, AND IMAGE PROCESSING DEVICE

(71) Applicant: NIKON CORPORATION, Tokyo (JP)

(72) Inventors: Yasushi Tanabe, Fujisawa (JP); Mariko Hirokawa, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 243 days.

(21) Appl. No.: 17/072,321

(22) Filed: Oct. 16, 2020

(65) Prior Publication Data
US 2021/0035294 A1 Feb. 4, 2021

Related U.S. Application Data

(63) Continuation of application No. PCT/JP2019/016653, filed on Apr. 18, 2019.

(30) Foreign Application Priority Data

Apr. 18, 2018 (JP) .............................. JP2018-080274

(51) Int. Cl.
*G06T 7/00* (2017.01)
*G06T 7/73* (2017.01)
*G06V 40/18* (2022.01)

(52) U.S. Cl.
CPC .............. *G06T 7/0012* (2013.01); *G06T 7/73* (2017.01); *G06V 40/18* (2022.01); *G06T 2207/30041* (2013.01); *G06T 2207/30104* (2013.01); *G06V 2201/03* (2022.01)

(58) Field of Classification Search
CPC ..................... G06T 7/0012; G06T 7/73; G06T 2207/30041; G06T 2207/30104; G06V 40/18; G06V 2201/03; A61B 3/10; A61B 3/12; A61B 3/00
See application file for complete search history.

(56) References Cited

U.S. PATENT DOCUMENTS

| 5,868,134 A | 2/1999 | Sugiyama |
| 8,356,901 B2* | 1/2013 | Spaide ..................... A61B 3/15 |
| | | 351/221 |
| 11,284,791 B2* | 3/2022 | Tanabe ................. A61B 3/0058 |
| 2001/0028438 A1* | 10/2001 | Matsumoto ............ A61B 3/152 |
| | | 351/206 |

(Continued)

FOREIGN PATENT DOCUMENTS

JP H07-136122 A 5/1995

OTHER PUBLICATIONS

Shields CL, Shields JA, De Potter P. Patterns of indocyanine green videoangiography of choroidal tumours. Br J Ophthalmol. Mar. 1995;79(3):237-45. doi: 10.1136/bjo.79.3.237. PMID: 7703202; PMCID: PMC505071.*

(Continued)

*Primary Examiner* — Shefali D Goradia
(74) *Attorney, Agent, or Firm* — Foley & Lardner LLP

(57) ABSTRACT

A feature value related to a positional relationship between a vortex vein position and a characteristic point on a fundus image is computed.
The image processing method provided includes a step of analyzing a choroidal vascular image and estimating a vortex vein position, and a step of computing a feature value indicating a positional relationship between the vortex vein position and a position of a particular site on a fundus.

17 Claims, 13 Drawing Sheets

(56) References Cited

U.S. PATENT DOCUMENTS

| | | | |
|---|---|---|---|
| 2013/0194546 A1* | 8/2013 | Iwase | A61B 3/14 351/246 |
| 2014/0307228 A1* | 10/2014 | Ohban | A61B 3/12 351/208 |
| 2018/0052972 A1* | 2/2018 | Hipsley | G06T 17/20 |
| 2020/0383965 A1* | 12/2020 | Zarnitsyn | A61K 9/0048 |
| 2021/0022600 A1* | 1/2021 | Tanabe | G06T 7/62 |
| 2021/0022606 A1* | 1/2021 | Tanabe | G06T 7/73 |
| 2022/0230307 A1* | 7/2022 | Hirokawa | A61B 3/0058 |

OTHER PUBLICATIONS

Mrejen, Sarah, and Richard F. Spaide. "Optical coherence tomography: imaging of the choroid and beyond." Survey of ophthalmology 58.5 (2013): 387-429.*

* cited by examiner

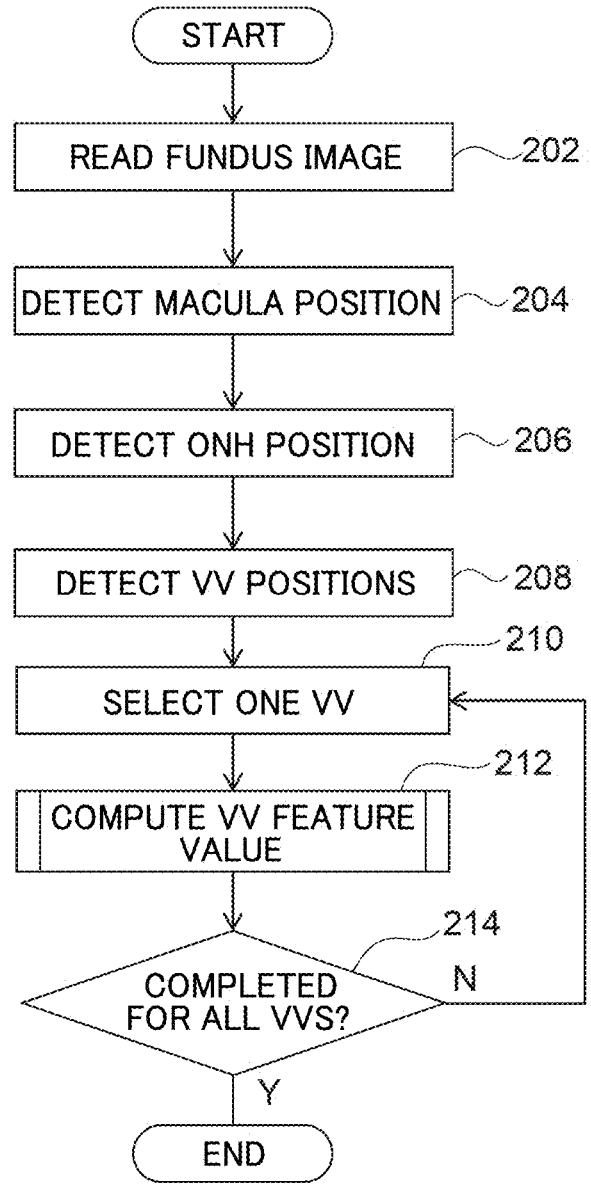

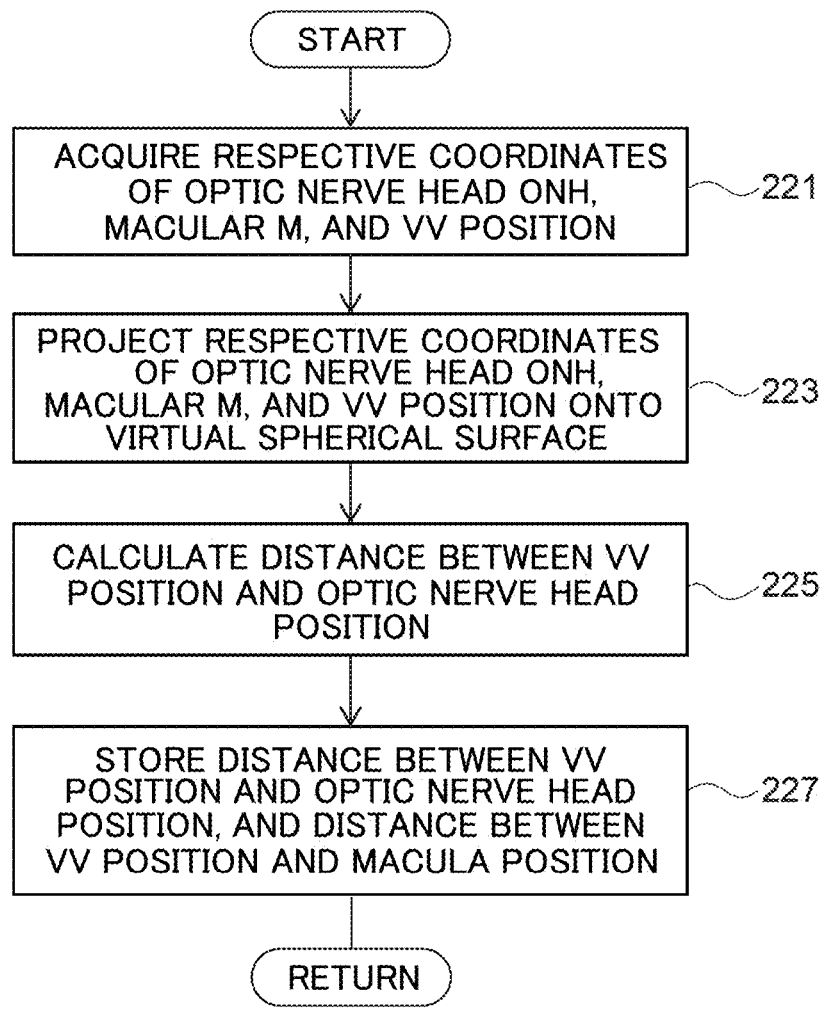

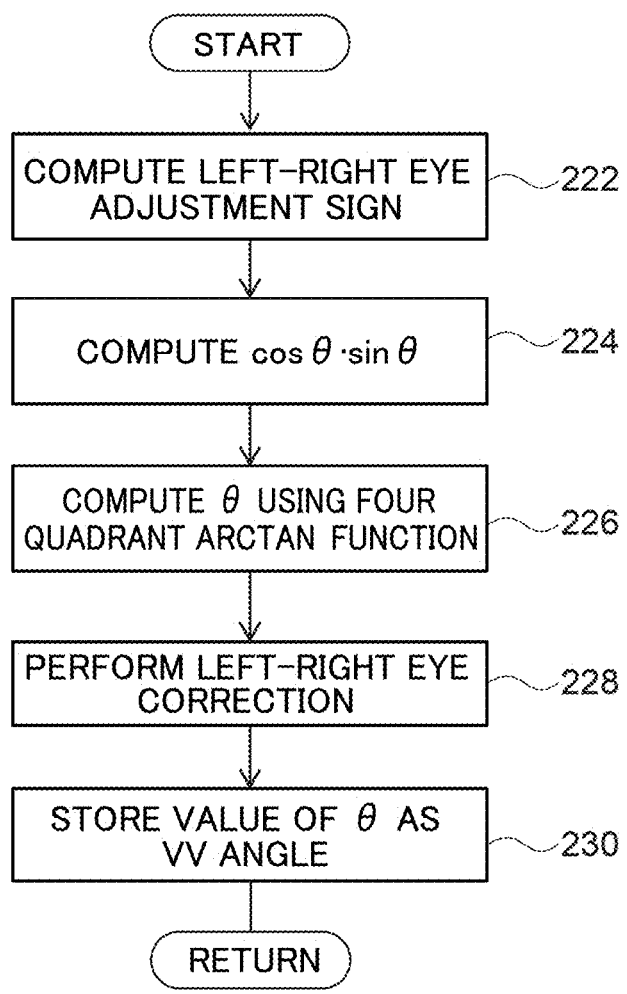

IMAGE PROCESSING METHOD, PROGRAM, AND IMAGE PROCESSING DEVICE

CROSS-REFERENCE TO RELATED APPLICATIONS

This application is a continuation application of International Application No. PCT/JP2019/016653 filed Apr. 18, 2019, the disclosure of which is incorporated herein by reference in its entirety. Further, this application claims priority from Japanese Patent Application No. 2018-080274, filed Apr. 18, 2018, the disclosure of which is incorporated herein by reference in its entirety.

TECHNICAL FIELD

Technology disclosed herein relates to an image processing method, a program, and an image processing device.

RELATED ART

Technology is disclosed in Japanese Patent Application Laid-Open (JP-A) No. H7-136122 for detecting positions of an optic nerve head portion and a macular portion in a fundus image. There has hitherto been demand to perform analysis of fundus diseases using fundus images.

SUMMARY

An image processing method of a first aspect of technology disclosed herein includes a step of analyzing a choroidal vascular image and estimating a vortex vein position, and a step of computing a feature value indicating a positional relationship between the vortex vein position and a position of a particular site on a fundus.

A program of a second aspect of technology disclosed herein causes a computer to execute the image processing method of the first aspect.

An image processing device of a third aspect of technology disclosed herein is an ophthalmic device including a storage device configured to store a program causing a processing device to execute an image processing method, and a processing device configured to execute the image processing method by executing the program stored in the storage device. The image processing method is the image processing method of the first aspect.

An image processing device of a fourth aspect of technology disclosed herein is an image processing device including a processing device for executing an image processing method. The processing device is configured to execute a step of analyzing a choroidal vascular image and estimating a vortex vein position, and a step of computing a feature value indicating a positional relationship between positions of the vortex vein position and a position of a particular site on a fundus.

BRIEF DESCRIPTION OF DRAWINGS

FIG. 5 is flowchart of an image processing program.

FIG. 6A is a flowchart of a VV distance computation processing program in VV feature value computation processing at step 212 in FIG. 5.

FIG. 6B is a flowchart of a VV angle computation processing program in VV feature value computation processing at step 212 in FIG. 5.

DETAILED DESCRIPTION

Detailed explanation follows regarding exemplary embodiments of the present invention, with reference to the drawings. In the following, for ease of explanation, a scanning laser ophthalmoscope is referred to as an "SLO".

Figure 1:
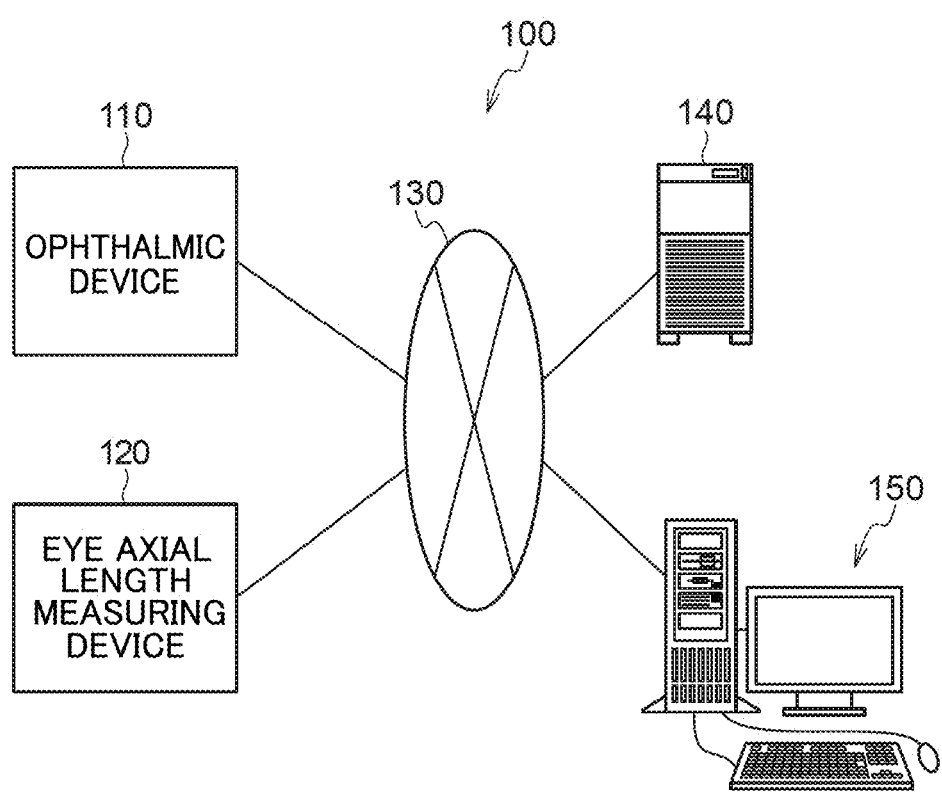
FIG. 1 is a block diagram illustrating an ophthalmic system 100.

The configuration of an ophthalmic system 100 will now be described with reference to FIG. 1. As illustrated in FIG. 1, the ophthalmic system 100 includes an ophthalmic device 110, an eye axial length measuring device 120, a management server device (hereinafter referred to as "management server") 140, and an image display device (hereinafter referred to as "image viewer") 150. The ophthalmic device 110 acquires fundus images. The eye axial length measuring device 120 measures the eye axial length of a patient. The management server 140 stores plural fundus images and eye axial lengths obtained by imaging the fundi of plural patients using the ophthalmic device 110, stored associated with respective patient IDs.

The ophthalmic device 110, the eye axial length measuring device 120, the management server 140, and the image viewer 150 are connected to each other over a network 130.

Note that other ophthalmic instruments (instruments for performing examinations such as optical coherence tomography (OCT) measurement, field of view measurement and intraocular pressure measurement) and a diagnostic support device that performs image analysis using artificial intelligence may be connected over the network 130 to the ophthalmic device 110, the eye axial length measuring device 120, the management server 140, and the image viewer 150.

Figure 2:
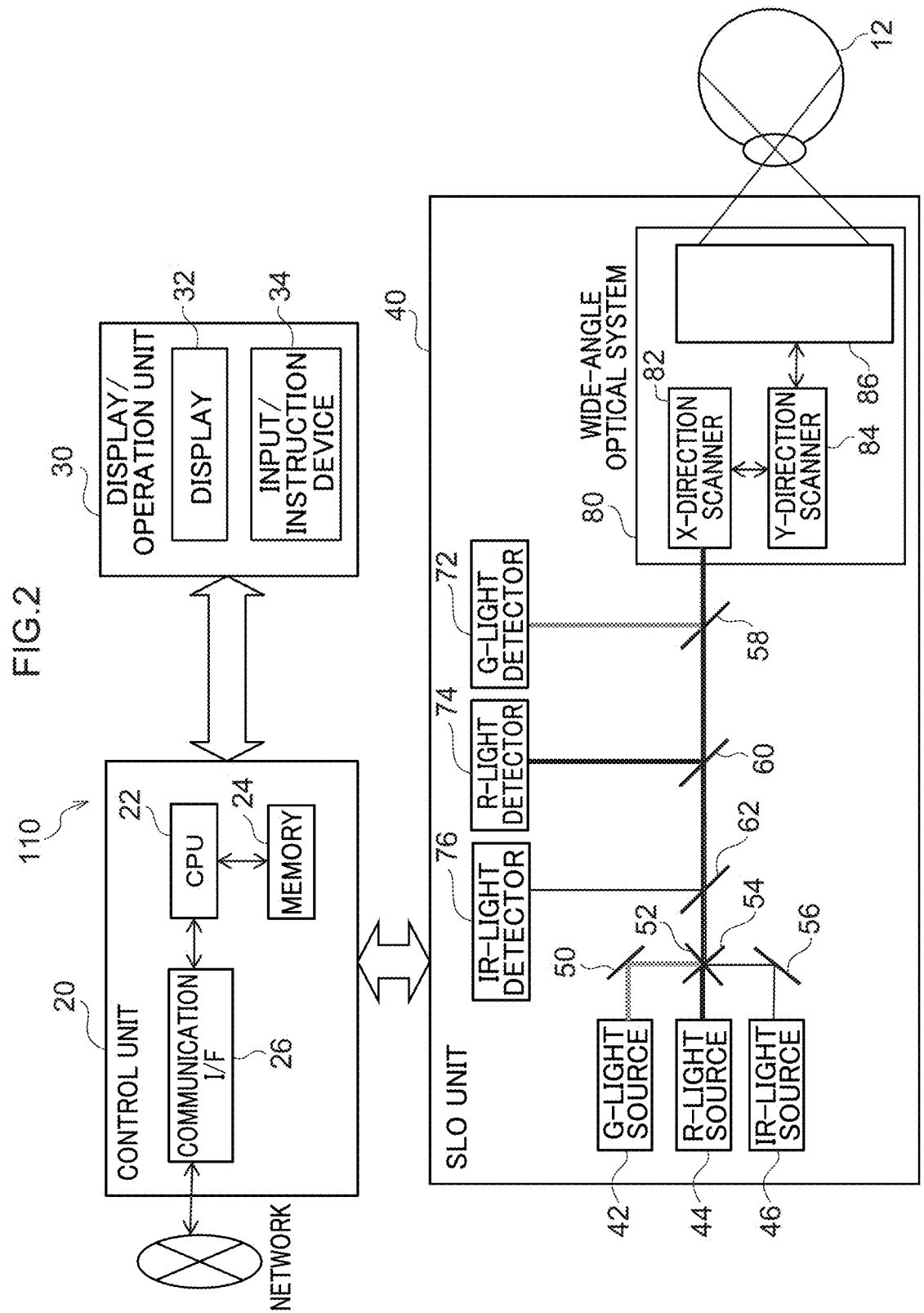
FIG. 2 is a schematic configuration diagram illustrating an overall configuration of an ophthalmic device 110.

Explanation follows regarding a configuration of the ophthalmic device 110, with reference to FIG. 2. As illustrated in FIG. 2, the ophthalmic device 110 includes a control unit 20, a display/operation unit 30, and an SLO unit 40, and images the posterior segment (fundus) of the examined eye 12. Furthermore, a non-illustrated OCT unit may be provided for acquiring OCT data of the fundus.

The control unit 20 includes a CPU 22, memory 24, a communication interface (I/F) 26, and the like. The display/operation unit 30 is a graphical user interface to display images obtained by imaging, and to receive various instructions including an imaging instruction. The display/operation unit 30 also includes a display 32 and an input/instruction device 34 such as a touch panel.

The SLO unit 40 includes a light source 42 for green light (G-light: wavelength 530 nm), a light source 44 for red light (R-light: wavelength 650 nm), and a light source 46 for infrared radiation (IR-light (near-infrared light): wavelength 800 nm). The light sources 42, 44, 46 respectively emit light as commanded by the control unit 20.

The SLO unit 40 includes optical systems 50, 52, 54 and 56 that reflect or transmit light from the light sources 42, 44 and 46 in order to guide the reflected light into a single optical path. The optical systems 50 and 56 are mirrors, and the optical systems 52 and 54 are beam splitters. The G-light is reflected by the optical systems 50 and 54, the R-light is transmitted through the optical systems 52 and 54, and the IR-light is reflected by the optical systems 52 and 56, such that all are guided into a single optical path.

The SLO unit 40 includes a wide-angle optical system 80 for two-dimensionally scanning light from the light sources 42, 44, 46 across the posterior segment (fundus) of the examined eye 12. The SLO unit 40 includes a beam splitter 58 that, from out of the light from the posterior segment (fundus) of the examined eye 12, reflects the G-light and transmits light other than the G-light. The SLO unit 40 includes a beam splitter 60 that, from out of the light transmitted through the beam splitter 58, reflects the R-light and transmits light other than the R-light. The SLO unit 40 includes a beam splitter 62 that, from out of the light that has passed through the beam splitter 60, reflects IR-light. The SLO unit 40 is provided with a G-light detection element 72 that detects the G-light reflected by the beam splitter 58, an R-light detection element 74 that detects the R-light reflected by the beam splitter 60, and an IR-light detection element 76 that detects IR-light reflected by the beam splitter 62.

The wide-angle optical system 80 includes an X-direction scanning device 82 configured by a polygon mirror to scan the light from the light sources 42, 44, 46 in an X direction, a Y-direction scanning device 84 configured by a galvanometer mirror to scan the light from the light sources 42, 44, 46 in a Y direction, and an optical system 86 including a non-illustrated slit mirror and elliptical mirror to widen the angle over which the light is scanned. The optical system 86 is capable of achieving a field of view (FOV) of the fundus with a larger angle than in conventional technology, enabling a fundus region to be imaged over a wider range than when employing conventional technology. More specifically, a fundus region can be imaged over a wide range of approximately 120 degrees of external light illumination angles from outside the examined eye 12 (in practice approximately 200 degrees about a center O of the eyeball of the examined eye 12 as a reference position for an internal light illumination angle capable of being imaged in practice by illuminating the fundus of the examined eye 12 with scanning light). The optical system 86 may be configured employing plural lens sets instead of a slit mirror and elliptical mirror. Each scanning device of the X-direction scanning device 82 and the Y-direction scanning device 84 may also be a scanning device employing two-dimensional scanners configured by MEMS mirrors.

A configuration may employ a system using an elliptical mirror as described in International Applications PCT/JP2014/084619 or PCT/JP2014/084630 in cases in which a system including a slit mirror and an elliptical mirror is used as the optical system 86. The respective disclosures of International Application PCT/JP2014/084619 (International Publication WO2016/103484) filed on Dec. 26, 2014 and International Application PCT/JP2014/084630 (International Publication WO2016/103489) filed on Dec. 26, 2014 are incorporated by reference herein in their entireties.

Note that when the ophthalmic device 110 is installed on a horizontal plane, the "X direction" corresponds to a horizontal direction and the "Y direction" corresponds to a direction perpendicular to the horizontal plane. A direction connecting the center of the pupil of the anterior eye portion of the examined eye 12 and the center of the eyeball is referred to as the "Z direction". The X direction, the Y direction, and the Z direction are accordingly perpendicular to one another.

A color fundus image is obtained by imaging the fundus of the examined eye 12 using G-light and R-light simultaneously. More specifically, the control unit 20 controls the light sources 42, 44 such that the light sources 42, 44 emit light at the same time, and scans the G-light and R-light across the fundus of the examined eye 12 using the wide-angle optical system 80. G-light reflected from the fundus of the examined eye 12 is detected by the G-light detection element 72, and image data of a second fundus image (a G fundus image) is generated by the CPU 22 of the ophthalmic device 110. Similarly, R-light reflected from the fundus of the examined eye 12 is detected by the R-light detection element 74, and image data of a first fundus image (a R fundus image) is generated by the CPU 22 of the ophthalmic device 110. In cases in which IR-light is illuminated, IR-light reflected from the fundus of the examined eye 12 is detected by the IR-light detection element 76, and image data of an IR fundus image is generated by the CPU 22 of the ophthalmic device 110.

The CPU 22 of the ophthalmic device 110 mixes a first fundus image (R fundus image) and a second fundus image (G fundus image) together at a specific ratio and displays the resulting color fundus image on the display 32. Note that a configuration may be adopted in which instead of the color fundus image, the first fundus image (R fundus image), the second fundus image (G fundus image) or an IR fundus image is displayed.

Image data of the first fundus image (R fundus image), image data of the second fundus image (G fundus image), and image data of the IR fundus image is sent from the ophthalmic device 110 to the management server 140 through a communication IF 166. The various fundus images are utilized to generate a choroidal vascular image.

The eye axial length measuring device 120 in FIG. 1 has two modes for measuring the eye axial length, this being the length of the examined eye 12 in an eye axial direction (Z direction), namely a first mode and a second mode. In the first mode, light from a non-illustrated light source is guided into the examined eye 12, and interference light generated by interference between reflected light from the fundus and reflected light from the cornea is received, and the eye axial length is measured based on an interference signal represented by the interference light received. The second mode is a mode in which non-illustrated ultrasound waves are employed to measure the eye axial length. The eye axial length measuring device 120 transmits the eye axial length measured using either the first mode or the second mode to the management server 140. The eye axial length may be measured using both the first mode and the second mode, in which case an average of the eye axial lengths measured by the two modes is transmitted to the management server 140 as the eye axial length. The eye axial length is saved as patient information in the management server 140 as one item of data about the examinee, and is also used in fundus image analysis.

Figure 3:
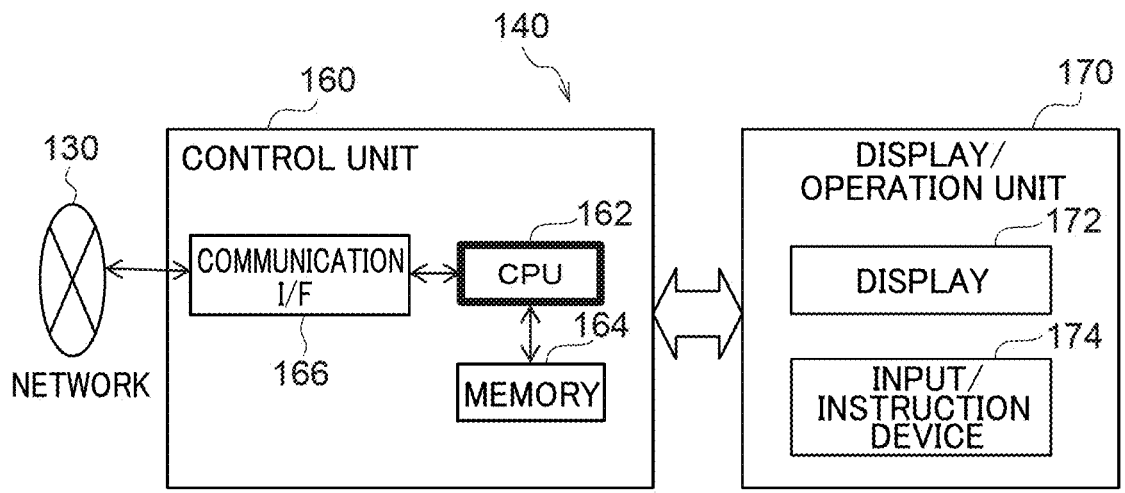
FIG. 3 is a block diagram of a configuration of an electrical system of a management server 140.

Next, a configuration of the management server 140 will be described with reference to FIG. 3. As illustrated in FIG. 3, the management server 140 includes a control unit 160, and a display/operation unit 170. The control unit 160 is equipped with a computer including a CPU 162, memory 164 configured by a storage device, a communication interface (I/F) 166, and the like. Note that an image processing program is stored in the memory 164. The display/operation unit 170 is a graphical user interface for displaying images and for receiving various instructions. The display/operation unit 170 includes a display 172 and an input/instruction device 174 such as a touch panel.

The configuration of the image viewer 150 is similar to that of the management server 140, and so description thereof is omitted.

Figure 4:
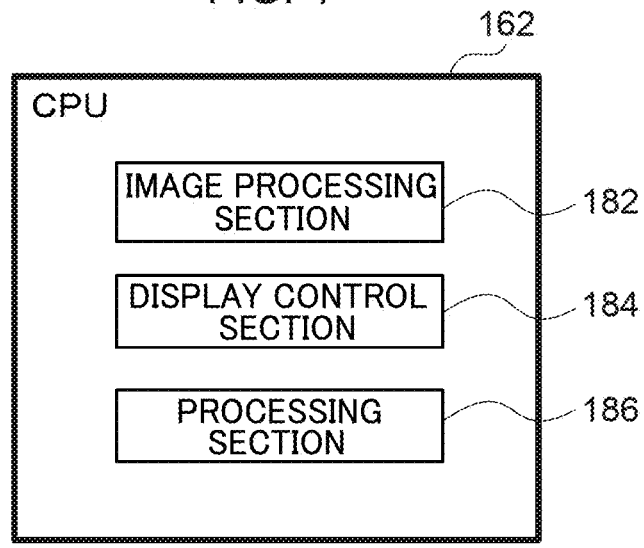
FIG. 4 is a block diagram illustrating functions of a CPU 162 of a management server 140.

Next, with reference to FIG. 4, description follows regarding each of various functions implemented by the CPU 162 of the management server 140 executing the image processing program. The image processing program includes an image processing function, a display control function, and a processing function. By the CPU 162 executing the image processing program including each of these functions, the CPU 162 functions as an image processing section 182, a display control section 184, and a processing section 186, as illustrated in FIG. 4.

Next, with reference to FIG. 5, detailed description follows regarding image processing by the management server 140. The image processing illustrated in the flowchart of FIG. 5 is implemented by the CPU 162 of the management server 140 executing an image processing program.

The image processing program is executed by the management server 140 when generating a choroidal vascular image based on the image data of the fundus images imaged by the ophthalmic device 110. The choroidal vascular image is generated in the following manner.

First information contained in the first fundus image (R fundus image) and the second fundus image (G fundus image) will be described.

The structure of the eye is configured by the vitreous body covered by plural layers that each have a different structure. These plural layers include the retina, the choroid, and the sclera in sequence from the side closest to the vitreous body outward. R-light passes through the retina and travels as far as the choroid. Accordingly, the first fundus image (R fundus image) includes information relating to blood vessels (retinal blood vessels) present in the retina and information relating to blood vessels (choroidal blood vessels) present in the choroid. By contrast, G-light only travels as far as the retina. Accordingly, the second fundus image (G fundus image) includes information relating to the blood vessels (retinal blood vessels) present in the retina. Thus by extracting the retinal blood vessels from the second fundus image (G fundus image), a choroidal vascular image can be obtained by removing the retinal blood vessel from the first fundus image (R fundus image).

Figure 7:
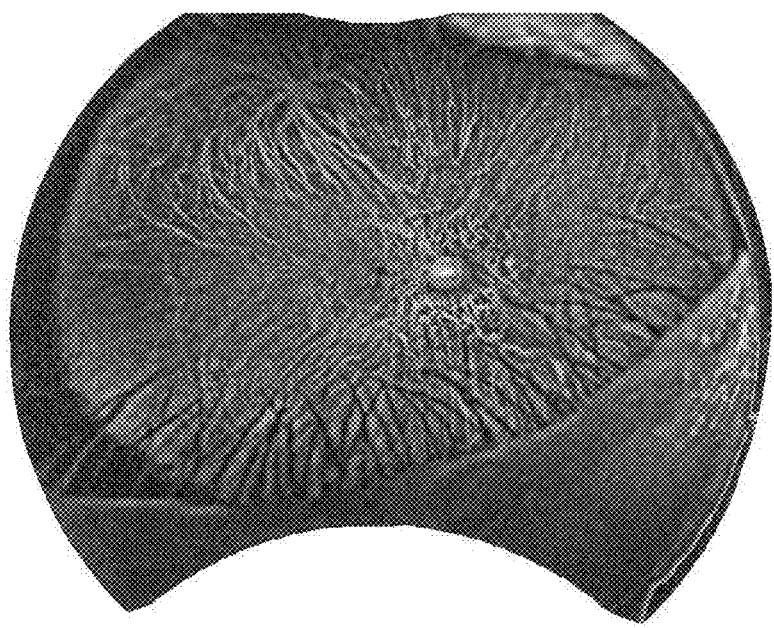
FIG. 7 is a diagram illustrating a choroidal vascular image.

Next, description follows regarding a method for generating a choroidal vascular image. The image processing section 182 of the management server 140 subjects the second fundus image (G fundus image) to black hat filter processing so as to extract the retinal blood vessels from the second fundus image (G fundus image). Next, the image processing section 182 removes the retinal blood vessels from the first fundus image (R fundus image) by performing in-painting processing employing the retinal blood vessels extracted from the second fundus image (G fundus image). Namely, processing is performed that uses position information relating to the retinal blood vessels extracted from the second fundus image (G fundus image) to infill the retinal blood vessel structures in the first fundus image (R fundus image) with the same pixel values to those of surrounding pixels. The image processing section 182 then subjects the image data of the first fundus image (R fundus image) from which the retinal blood vessels have been removed to contrast-limited adaptive histogram equalization (CLAHE), thereby emphasizing the choroidal blood vessels in the first fundus image (R fundus image). A choroidal vascular image as illustrated in FIG. 7 is obtained thereby. The generated choroidal vascular image is stored in the memory 164.

Moreover, although the choroidal vascular image is generated from the first fundus image (R fundus image) and the second fundus image (G fundus image), and the image processing section 182 may next generate a choroidal vascular image employing the first fundus image (R fundus image) or the IR fundus image imaged with IR light. Regarding the method used to generate the choroidal fundus image, the disclosure of Japanese Patent Application No. 2018-052246, filed on Mar. 20, 2018, is incorporated in its entirety by reference herein.

At the start of the image processing program, at step 202 of FIG. 5, the processing section 186 reads, as fundus images, the choroidal vascular image (see FIG. 7) and the G fundus image from the memory 164.

At step 204, the image processing section 182 estimates the macular position from the G fundus image. Specifically, the macular is a dark region in the G fundus image, and so the image processing section 182 detects a region of a specific number of pixels having the lowest pixel values in the G fundus image read as described above as the position of the macular.

At step 206, the image processing section 182 detects the position of the optic nerve head in the G fundus image. Specifically, the image processing section 182 detects the optic nerve head in the G fundus image by performing pattern matching on the G fundus image read as described above to predetermined optic nerve head images. Moreover, since the optic nerve head is the brightest region in the G fundus image, a region of a specific number of pixels with the highest pixel values in the G fundus image read as described above may be detected as the position of the optic nerve head.

The choroidal vascular image is created by processing the R fundus image and the G fundus image as described above. Thus by overlaying the coordinate system of the G fundus image onto the coordinate system of the choroidal vascular image, each of the positions in the coordinate system of the G fundus image is the same as each of the positions in the coordinate system of the choroidal vascular image. The positions on the choroidal vascular image that are equivalent to the respective positions of the macular and the optic nerve head detected in the G fundus image are accordingly the respective positions of the macular and the optic nerve head.

Thus in the processing of step 204, the position of the macular may be detected in the choroidal vascular image instead of in the G fundus image. Similarly, in the processing of step 206, the position of the optic nerve head may be detected in the choroidal fundus image instead of in the G fundus image.

At step 208, the image processing section 182 detects the position of vortex veins (hereafter VV) in the choroidal vascular image. Vortex veins VV are drains for blood that flowed into the choroid, with from four to six thereof being present on the equator of the eyeball toward the posterior pole of the eyeball.

The image processing section 182 finds the blood vessel running direction at each of the pixels in the choroidal vascular image. Specifically, the image processing section 182 repeatedly performs the following processing on all the pixels. Namely, the image processing section 182 sets a region (cell) configured by plural pixels around a given pixel at the center. Next, the image processing section 182 calculates a brightness gradient direction for each pixel of the cell (expressed as an angle from 0° to just under 180°. Note that 0° is defined as a direction of a straight line (horizontal line)) based on the brightness values of the pixels surrounding the pixel being calculated. The gradient direction calculation is performed for all of the pixels in the cell.

Next, in order to create a histogram with nine bins (bin widths of)20° of gradient direction centered on 0°, 20°, 40°, 60°, 80°, 100°, 120°, 140°, and 160°, the number of pixels inside the cell that have a gradient direction corresponding to each of the bins is counted. The width of a single bin in the histogram is 20°, and the 0° bin is set with the number (count value) of pixels in the cell having a gradient direction of from 0° up to but not including 10°, or a gradient direction of from 170° up to but not including 180°. The 20° bin is set with the number (count value) of pixels in the cell having a gradient direction of from 10° up to but not including 30°. The count values for the bins 40°, 60°, 80°, 100°, 120°, 140°, and 160° are set in a similar manner. Due to there being nine bins in the histogram, the blood vessel running direction at each of the pixels is defined as being in one of nine direction types. Note that the resolution of the blood vessel running direction can be raised by narrowing the width of each bin and increasing the number of bins. The count values of each of the bins (the vertical axis in the histogram) is normalized, and a histogram is created for each analysis point.

Next, the image processing section 182 identifies the blood vessel running direction at each analysis point from the histogram. Specifically, the bin with the angle having the smallest count value)(60°) is identified, and 60°, which is the gradient direction of the identified bin, is identified as the blood vessel running direction of the pixel. The gradient direction having the smallest count is taken as the blood vessel running direction for the following reason. There is a small brightness gradient in the blood vessel running direction, however, there is a larger brightness gradient in other directions (for example, there is a large difference in brightness between blood vessels and tissue other than blood vessels). Thus when the respective histograms of brightness gradient have been created for each of the pixels, then the count value becomes small for the bin along the blood vessel running direction. Histograms are similarly created for each of the pixels in the choroidal vascular image, and the blood vessel running direction is computed at each of the pixels. The computed blood vessel running directions at each of the pixels are stored in the memory 164.

The image processing section 182 then sets an initial position of imaginary particles at M individual positions at uniform spacings in the choroidal vascular image vertically and at N individual positions therein horizontally, namely a total of L individual positions. For example, if M=10 and N=50, then a total of L=500 individual initial positions are set.

Furthermore, the image processing section 182, acquires the blood vessel running direction of a first position (one of the L individual positions), moves the imaginary particle by a specific distance along the acquired blood vessel running direction, repeats acquisition of the blood vessel running direction but this time at the position moved to, and then moves the imaginary particle by the specific distance along this acquired blood vessel running direction. Such movements of a specific movement distance along the acquired blood vessel running direction are repeated a preset number of times. The above processing is executed for all of the L individual positions. At the point in time when all of the L individual imaginary particles have been moved the preset number of times, a point where a given number of imaginary particles or more have collected together is detected as a VV position.

The number of VVs detected and the VV position information (the coordinates indicating the VV positions in the choroidal vascular image) are stored in the memory 164.

At step 210, the image processing section 182 increments a variable n by one, and selects a VV (one VV) discriminated by the variable n. The initial value of n is zero.

At step 212, the image processing section 182 computes a first feature value (VV distance) related to a distance and a second feature value (VV angle) related to an angle for the respective VV. The first feature value is a distance between the VV and a characteristic structure on the fundus, and is a distance between the macula and the VV, or is a distance between the optic nerve head and the VV. The second feature value is an angle identified by three points, the VV, a characteristic first structure on the fundus, and a characteristic second structure on the fundus, and is an angle turned through when traveling from the VV to the macula and then on toward the optic nerve head position, or an angle turned through when traveling from the VV to the macular and then on toward the optic nerve head.

At step 214, the image processing section 182 determines whether or not processing has been completed for all VVs by determining whether or not the variable n is the same as the total number N of the VVs that were detected. In cases in which the image processing section 182 has determined that the processing has not been completed for all the VVs, then image processing returns to step 210, the variable n is incremented by one, and the above processing (steps 210 to 214) is repeated.

The image processing of the flowchart of FIG. 5 is ended in cases in which the image processing section 182 has determined processing to be complete for all VVs.

Next explanation follows regarding computation processing at step 212 for the two types of VV feature value, the first feature value (VV distance) and the second feature value (VV angle). The computation processing of step 212 includes VV distance computation processing illustrated in FIG. 6A, and the VV angle computation processing illustrated in FIG. 6B.

Explanation first follows regarding the VV distance computation processing, with reference to FIG. 6A.

At step 221, the image processing section 182 acquires the respective coordinates of the optic nerve head ONH, macular M, and VV positions on the choroidal fundus image.

Figure 10:
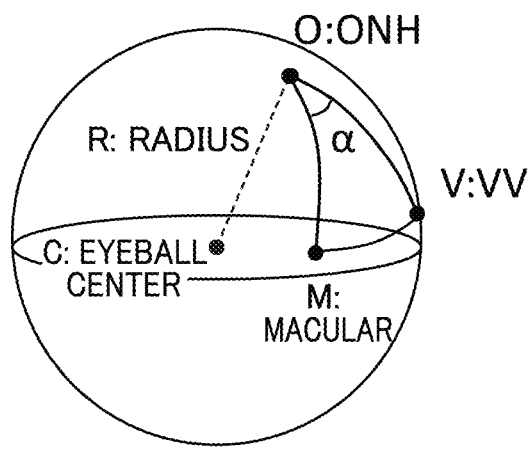
FIG. 10 is a diagram illustrating a macular position M, an optic nerve head ONH position O, and a VV position V as positions on a spherical surface with an eyeball center C at the center.

Next, at step 223, the image processing section 182 projects the respective coordinates of the optic nerve head ONH, macular M, and VV positions onto a virtual spherical surface as illustrated in FIG. 10. The virtual spherical surface illustrated in FIG. 10 is a spherical surface centered on eyeball center C, and having a radius R (wherein 2R is the eye axial length). The position of the VV is projected onto the spherical surface at V, the position of the optic nerve head ONH is projected thereon at O, and the position of the macular is projected thereon at M.

Taking this virtual spherical surface as a model of the eyeball, at step 225 the image processing section 182 calculates a distance on a great circle between two points on the spherical surface as the VV distance. Namely, a great circle is defined as a section arising from cutting the sphere so as to pass through the sphere center O, and a great circle distance is defined as the length of an arc on the great circle connecting two points (the VV position: V and the optic nerve head position: O, or the VV position: V and the macular: M) for which the distance is measured on the spherical surface. When the latitude and longitude on the virtual spherical surface of the VV position: V are expressed as (latitude $\theta 1$, longitude $\varphi 1$), and the latitude and longitude thereon of the optic nerve head position: O are expressed as (latitude $\theta 2$, longitude $\varphi 2$), then at step 223, the image processing section 182 calculates the VV distance between the VV position and the optic nerve head position, namely, the great circle distance OV, using spherical trigonometry.

$$R \cos^{-1}(\cos\theta_1 \cos\theta_2 \cos(\varphi_1-\varphi_2)+\sin\theta_1 \sin\theta_2) \quad \text{Equation 1}$$

At the present step 225, in cases in which the VV distance is the distance from the macula position M to the VV position V, the image processing section 182 may be configured to similarly calculate a distance between the VV position and the macula position, namely, the great circle distance MV.

At step 227, the image processing section 182 stores the computed VV distances, namely the VV distance between the VV position and the optic nerve head position (great circle distance OV) and the distance between the VV position and the macula position (great circle distance MV) in the memory 164.

When the flow illustrated in FIG. 6A has been completed, the VV feature value computation processing proceeds to the VV angle computation processing of FIG. 6B.

Next description follows regarding the VV angle computation processing.

Figure 8:
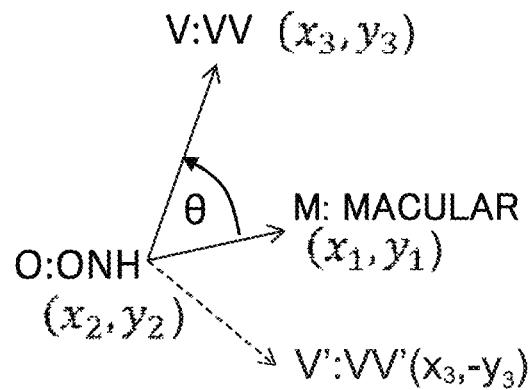
FIG. 8 is a diagram illustrating a macular M position, an optic nerve head ONH position, and a VV position.

As illustrated in FIG. 8, the VV angles are an angle $\theta$ turned through when traveling from the macular M position to the optic nerve head ONH position and on toward the VV position, and an angle turned through when traveling from the optic nerve head ONH position to the macular M position and on toward the VV position.

The method for computing the angle $\theta$ turned through when traveling from the macular M position to the optic nerve head ONH position and on toward the VV position may be by the following computation by conformal projection or computation by spherical trigonometry.

First description follows regarding computation of angle $\theta$ by conformal projection, with reference to FIG. 6B.

In a normal method of computation from an inner product, there is no discrimination between positive and negative computed angles, and it is not possible to discriminate between a VV on the upper hemisphere ($(x_3, y_3)$ in FIG. 8), and a VV' on the lower hemisphere $(x_3, -y_3)$. Moreover, in a method employing an arctan function, although there is a discrimination made between positive and negative, since the computation direction of $\theta$ is always constant (for example, counterclockwise), the values in the upper and lower hemispheres are reversed in the left and right eyes with reference to anatomical features (nose side/ear side). To address this matter, in the present exemplary embodiment a left-right eye adjustment sign $f_{sign}$ is employed so as to adjust the positive and the negative of the computed angle.

At step 222 of FIG. 6B, the image processing section 182 computes the left-right eye adjustment sign $f_{sign}$. As illustrated in FIG. 8, the macular M position is $(x_1, y_1)$, the optic nerve head ONH position is $(x_2, y_2)$, and the VV position is $(x_3, y_3)$.

The left-right eye adjustment sign $f_{sign}$ is set as:
$f_{sign}=+1$ (in cases in which $x_1>x_2$)
$f_{sign}=-1$ (in cases in which $x_1<x_2$)
This approach is adopted since it is possible to determine anatomically from the positions of the macular and the optic nerve head that when $x_1>x_2$ then this is the left eye and when $x_1<x_2$ then this is the right eye. Moreover, were there to be a case in which $x_1=x_2$, then in this case $f_{sign}=+1$.

At step 224, the image processing section 182 computes $\cos\theta$ and $\sin\theta$ based on the definitions of an inner product and cross product of vectors using Equation 2 and Equation 3. The angle $\theta$ turned through when traveling from the macular M position to the optic nerve head ONH position and on toward the VV position is an angle formed between a vector OM (the vector connecting the optic nerve head position O and the macula position M) and a vector OV (the vector connecting the optic nerve head position O to the vortex vein position V).

$$\cos\theta = \frac{\overrightarrow{OM}\cdot\overrightarrow{OV}}{|OM||OV|} \quad \text{Equation 2}$$

$$\sin\theta = \frac{(x_1-x_2)(y_3-y_2)-(x_3-x_2)(y_1-y_2)}{|OM||OV|} \quad \text{Equation 3}$$

At step 226, the image processing section 182 computes $\theta$ using in the following manner using a four quadrant arctan function.

$$\theta = a\tan 2(\sin\theta, \cos\theta) \quad \text{Equation 4}$$

Figure 9:
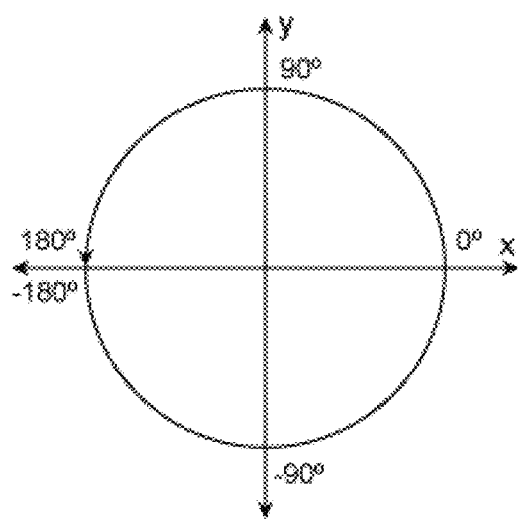
FIG. 9 is diagram illustrating a four quadrant arctan function.

$\theta$ found from the four quadrant arctan function does not only factor in the value of y/x, but, as illustrated in FIG. 9, also considers the sign of x in the respective four quadrants.

At step 228, the image processing section 182 performs left-right eye correction on the sign of the computed $\theta$ using the sign $f_{sign}$ in the following manner. At step 230, the image processing section 182 stores the value of $\theta$ found in this manner as the VV angle in the memory 164. The angle turned through when traveling from the optic nerve head ONH position to macular M position and on toward the VV position may be found in a similar manner.

$$\theta = \theta \cdot f_{sign} \quad \text{Equation 5}$$

Next, description follows regarding the method of computing the angle $\theta$ using spherical trigonometry.

As illustrated in FIG. 10, the macula position M, the optic nerve head ONH position O, and the VV position V are positions on the surface of a sphere having the eyeball center C at the center, and having a radius R wherein the eye axial length is 2R. An angle, denoted $\alpha$, at the apex O of a triangle OMV having apexes of the macula position M, the optic nerve head ONH position O, and the VV position V can be computed from:

$$\cos\alpha = \frac{(\overrightarrow{CO}\times\overrightarrow{CM})\cdot(\overrightarrow{CO}\times\overrightarrow{CV})}{|\overrightarrow{CO}\times\overrightarrow{CM}||\overrightarrow{CO}\times\overrightarrow{CV}|} \quad \text{Equation 6}$$

-continued $$\sin\alpha = \frac{|(\vec{CO}\times\vec{CM})\cdot(\vec{CO}\times\vec{CV})|}{|\vec{CO}\times\vec{CM}||\vec{CO}\times\vec{CV}|} \quad \text{Equation 7}$$

(wherein α lies in a range [0, π]).

As θ changes (in the range of open interval [−π, π], the value of α is computed by θ=α·$g_{sign}$, wherein $g_{sign}$ (positional relationship between macular M and optic nerve head ONH, positional relationship between VV position V and macular M)={1, −1}. The value of θ found in this manner is stored as the VV angle in the memory 164.

The image processing program includes one or other of a program to compute the VV angle from the conformal projection illustrated in FIG. 6B, or a program to compute the VV angles using spherical trigonometry as described above.

Next, description follows regarding data for a display screen in the choroidal vascular analysis mode. The management server 140 includes the following display screen data for the choroidal vascular analysis mode.

First, as described above, image data for the fundus images (the first fundus image (R fundus image) and the second fundus image (G fundus image)) is transmitted from the ophthalmic device 110 to the management server 140, and the management server 140 holds the image data for the fundus images (the first fundus image (R fundus image) and the second fundus image (G fundus image)). The management server 140 also holds the image data of the choroidal vascular image (see FIG. 7), and VV position, the optic nerve head ONH position, the macular M position, and the VV feature values. The VV feature values referred to above are the distance from the optic nerve head ONH position to the VV position, the distance from the macula position to the VV position, the angle θ turned through when traveling from the macular M position to the optic nerve head ONH position and on toward the VV position, and the angle turned through when traveling from the optic nerve head ONH position to the macular M position and on toward the VV position.

Moreover, personal information about a patient is also input to the ophthalmic device 110 when the fundus of the patient is being imaged. The personal information includes an ID, name, age, visual acuity, and the like of the patient. Moreover, information indicating whether the eye whose fundus is imaged is either the right eye or the left eye is also input when the fundus of the patient is being imaged. Furthermore, the imaging date/time is also input when the fundus of the patient is being imaged. Data for the personal information, right eye/left eye information, and imaging date/time is transmitted from the ophthalmic device 110 to the management server 140. The management server 140 holds the data for the personal information, right eye/left eye information, and imaging date/time. The management server 140 also holds data for the eye axial length.

As described above, the management server 140 holds the above data for the display screen of the choroidal vascular analysis mode.

However, the doctor in the room where the image viewer 150 is provided might sometimes want to know the state of the choroidal blood vessels when diagnosing the patient. In such cases the doctor uses the image viewer 150 to transmit an instruction to the management server 140 to transmit the data of the choroidal vascular analysis mode display screen. On receipt of such an instruction, the management server 140 transmits the choroidal vascular analysis mode display screen data to the image viewer 150. On receipt of the choroidal vascular analysis mode display screen data and based on the choroidal vascular analysis mode display screen data, the image viewer 150 displays the display screen 300 for the choroidal vascular analysis mode illustrated in FIG. 11 on a display.

Icons and buttons for instructing the generation of images, described later, are displayed on a display screen, described later, of the image viewer 150. When an ophthalmologist has clicked on an icon or the like, an instruction signal corresponding to the clicked icon or the like is transmitted from the image viewer 150 to the image management server 140. On receipt of the instruction signal from the image viewer 150, the management server 140 generates an image corresponding to the instruction signal and transmits image data of the generated image to the image viewer 150. The image viewer 150 that has received the image data from the image management server 140 then displays an image based on the received image data on a display. Display screen generation processing is performed in the management server 140 by the CPU 162 performing actions of a display screen generation program.

The management server 140 is an example of an "image processing device" of technology disclosed herein.

Figure 11:
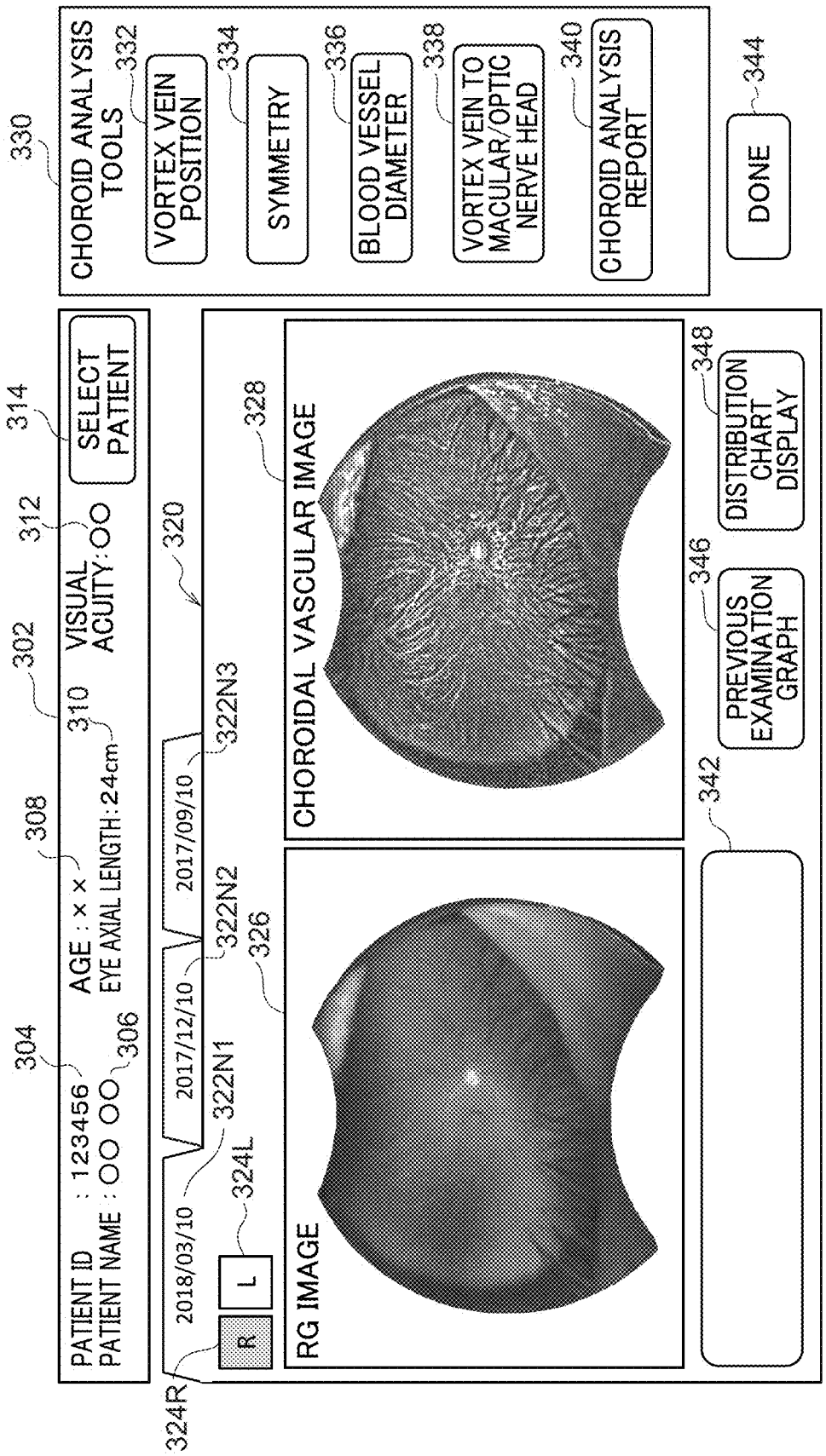
FIG. 11 is a diagram illustrating a display screen 300 in a choroidal vascular analysis mode.

Explanation follows regarding the choroidal vascular analysis mode display screen 300 as illustrated in FIG. 11. As illustrated in FIG. 11, the choroidal vascular analysis mode display screen 300 includes a personal information display field 302 to display personal information about a patient, an image display field 320, and a choroid analysis tool display field 330.

The personal information display field 302 includes a patient ID display field 304, a patient name display field 306, an age display field 308, an eye axial length display field 310, a visual acuity display field 312, and a patient selection icon 314. Various information is displayed in the patient ID display field 304, the patient name display field 306, the age display field 308, the eye axial length display field 310, and the visual acuity display field 312. Note that when the patient selection icon 314 is clicked, a list of patients is displayed on the display 172 of the image viewer 150, so as to let a user (ophthalmologist or the like) select the patient to be analyzed.

The image display field 320 includes an imaging date display field 322N1, a right eye information display field 324R, a left eye information display field 324L, an RG image display field 326, a choroidal vascular image display field 328, and an information display field 342. Note that the RG image is an image obtained by combining the first fundus image (R fundus image) and the second fundus image (G fundus image) by combining the magnitude of the respective pixel values together at a specific ratio (for example, 1:1).

The choroid analysis tool display field 330 contains plural choroid analysis tools to instruct processing to the image viewer 150 and includes, for example, a vortex vein position analysis icon 332, a symmetry icon 334, a blood vessel diameter icon 336, a vortex vein to macular/nerve head icon 338, and a choroid analysis report icon 340. The vortex vein position analysis icon 332 instructs identification of vortex vein positions. The symmetry icon 334 instructs analysis of vortex vein symmetry. The blood vessel diameter icon 336 instructs execution of a tool to analyze the diameters of the choroidal blood vessels. The vortex vein to macular/nerve head icon 338 instructs analysis of positioning and the like between the vortex vein, and the macular and optic nerve head. The choroid analysis report icon 340 instructs display of a choroid analysis report.

The example illustrated in FIG. 11 is able to display a RG image and a choroid image from when the fundus of the right eye (324R is illuminated) of a patient identified by the patient ID: 123456 was imaged on imaging days: Mar. 10, 2018; Dec. 10, 2017; and Sep. 10 2017. Note that the imaging date display field 322N1 has been clicked, and so the RG image and the choroid image that are displayed were those obtained by imaging on Mar. 10, 2018. Furthermore, the previous examination graph icon 346 and the distribution chart display icon 348 are also displayed in the image display field 320.

Figure 12:
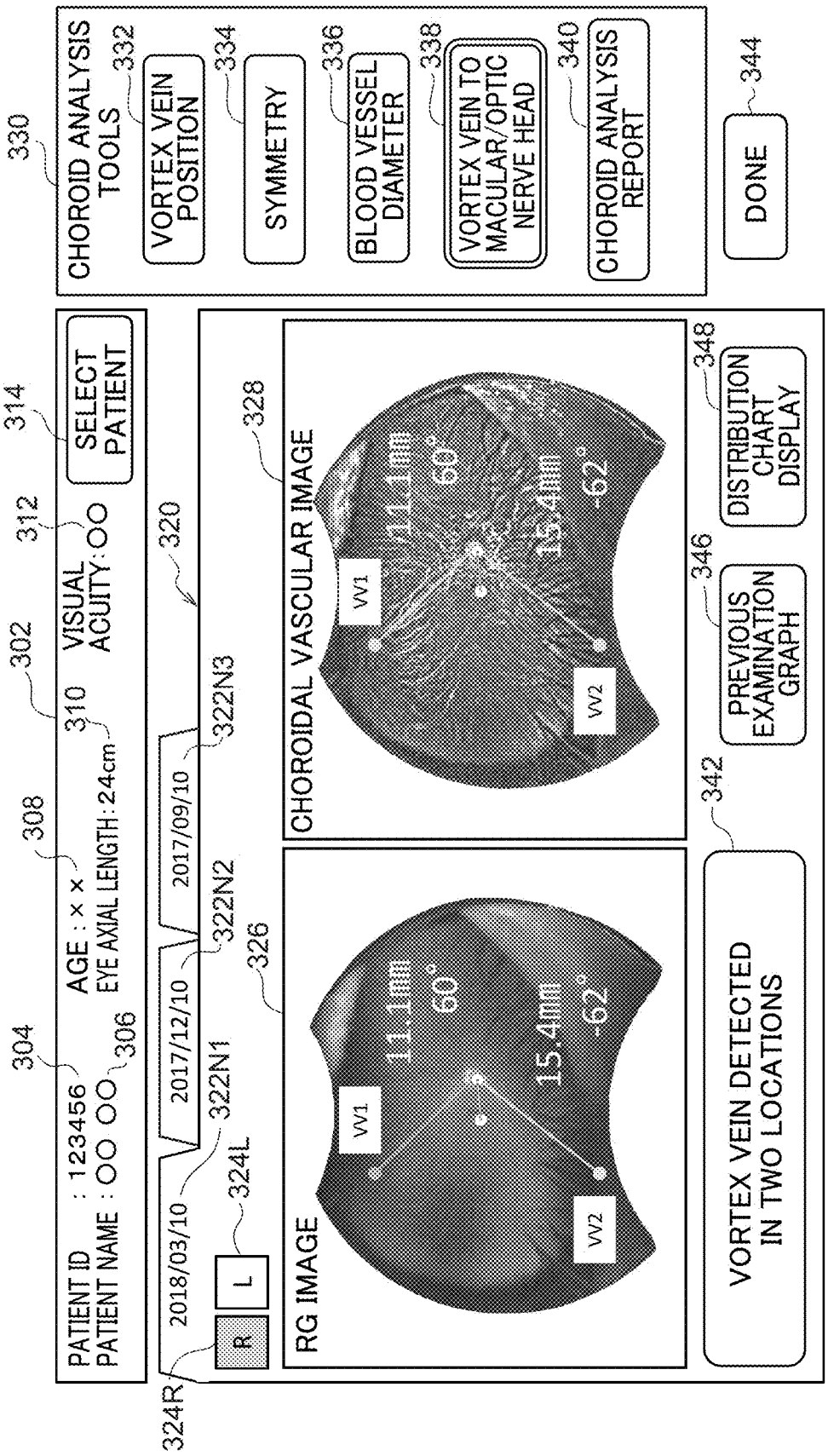
FIG. 12 is a diagram illustrating a display screen 300 on which positioning and the like between a vortex vein and a macular and an optic nerve head are displayed when a vortex vein to macular/optic nerve head icon 338 is clicked.

When the vortex vein to macular/nerve head icon 338 is clicked in the display screen 300 illustrated in FIG. 11, the positioning between the vortex vein, macular, and optic nerve head position is displayed as illustrated in FIG. 12. In the example illustrated in FIG. 12, VVs are detected in two locations, and a message "vortex vein detected in two locations" is displayed in the information display field 342. The respective positions of the optic nerve head, macular, and VVs are superimposed on the RG image in the RG image display field 326 and on the choroidal vascular image in the choroidal vascular image display field 328. The distances between the position of the optic nerve head ONH and the positions of the VV1, VV2 (VV1 distance=11.1 mm, VV2 distance=15.4 mm) are superimposed on the RG image in the RG image display field 326 and on the choroidal vascular image in the choroidal vascular image display field 328. The angles turned through when traveling from the macular M position to the optic nerve head ONH position and on toward the VV1, VV2 positions (VV1 angle=60°, VV2 angle=−62°) are superimposed on the RG image in the RG image display field 326 and on the choroidal vascular image in the choroidal vascular image display field 328.

Figure 13:
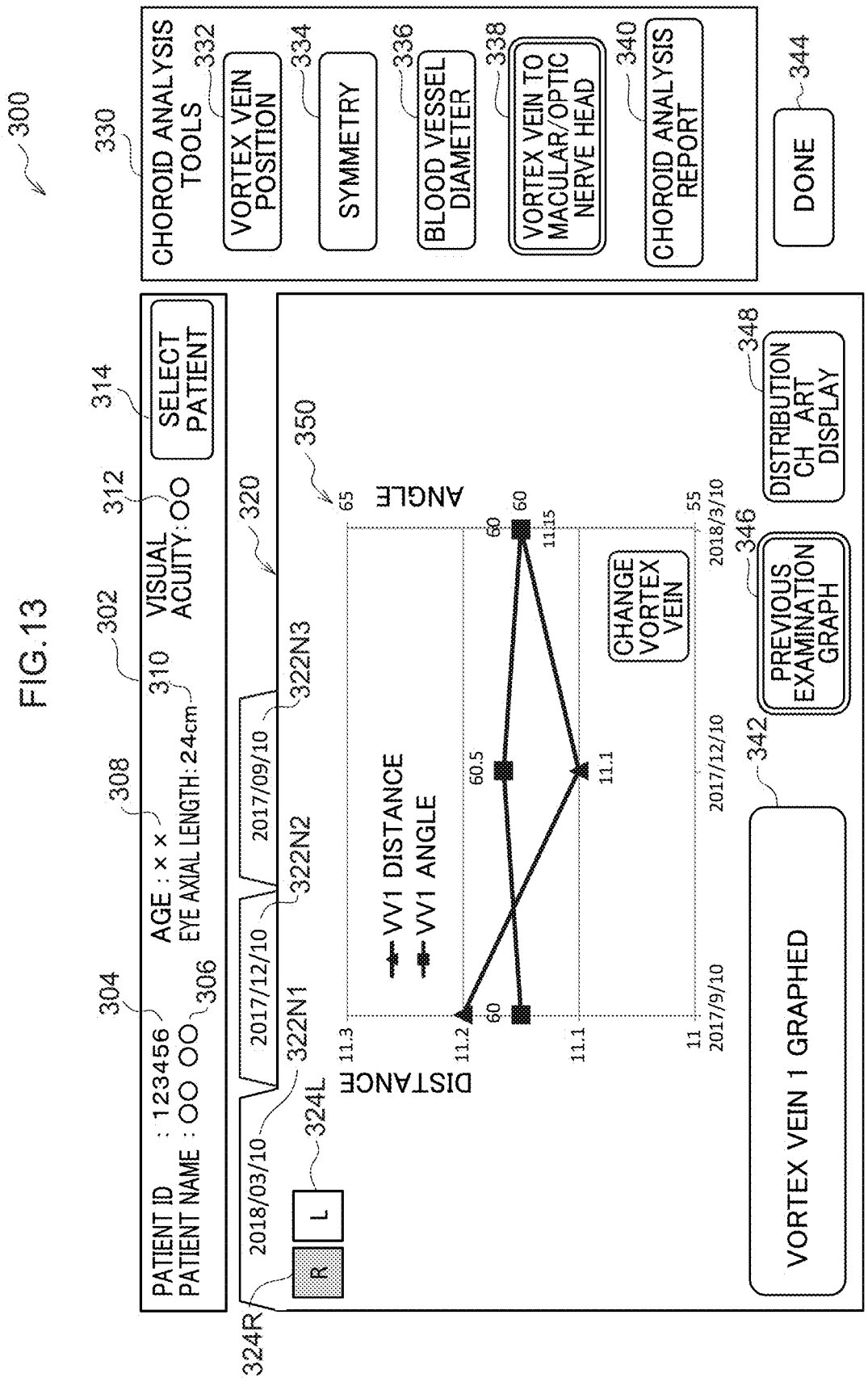
FIG. 13 is a diagram illustrating a display screen 300 on which a previous examination graph 350 is displayed when a previous examination graph icon 346 is clicked.

When the previous examination graph icon 346 is clicked in the display screen 300 of FIG. 12, the previous examination graph 350 illustrated in FIG. 13 is displayed. In the example illustrated in FIG. 13, the message "vortex vein 1 has been graphed" is displayed in the information display field 342. Previous examination graphs of the VV1 distance and VV1 angle for the vortex vein 1 (VV1) at each of the imaging days (Mar. 10, 2018; Dec. 10, 2017; and Sep. 10, 2017) is displayed in the previous examination graph 350.

Figure 14:
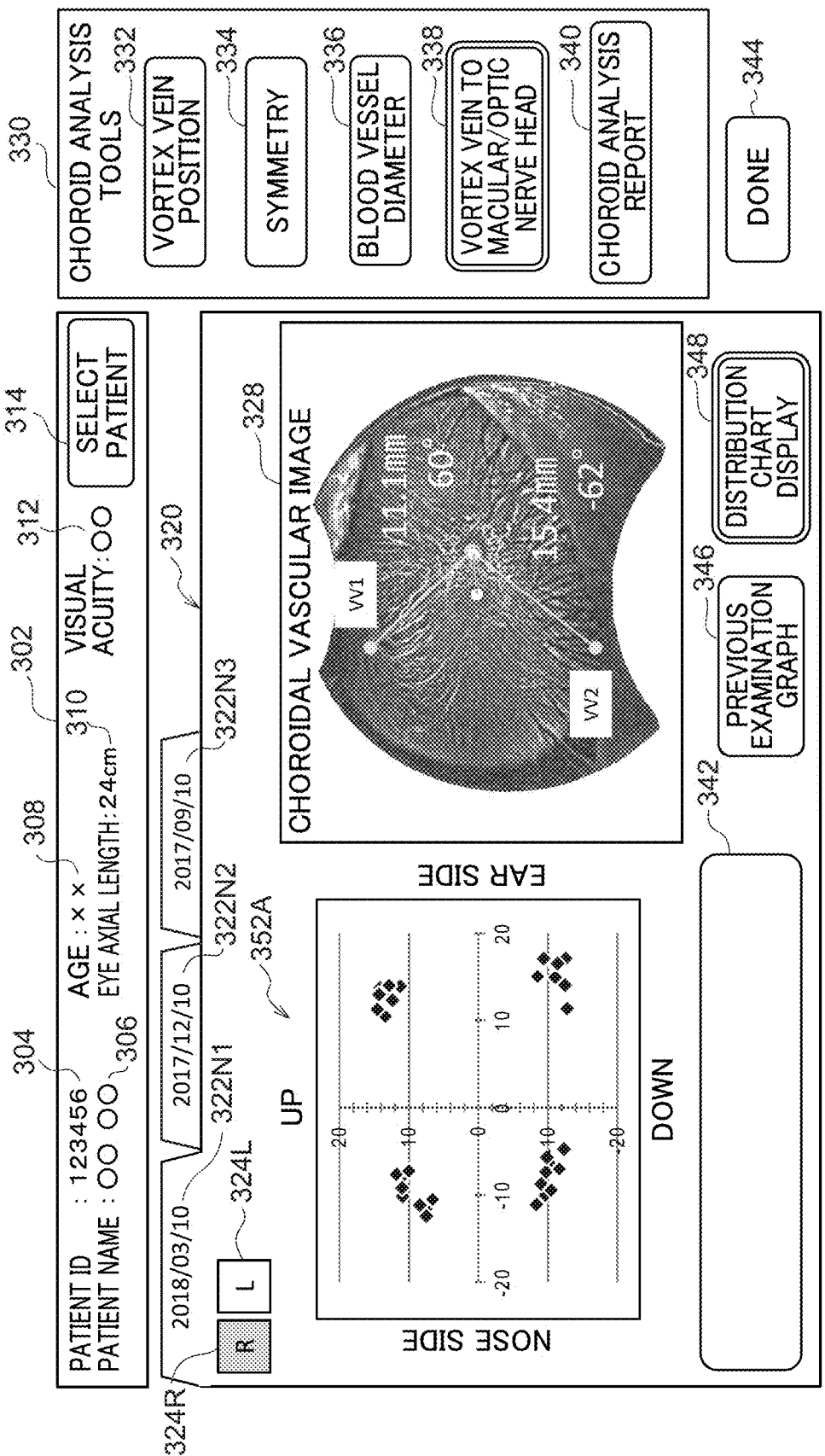
FIG. 14 is a diagram illustrating a display screen 300 on which a distribution chart 352A is displayed when a distribution chart display icon 348 is clicked.
Figure 15:
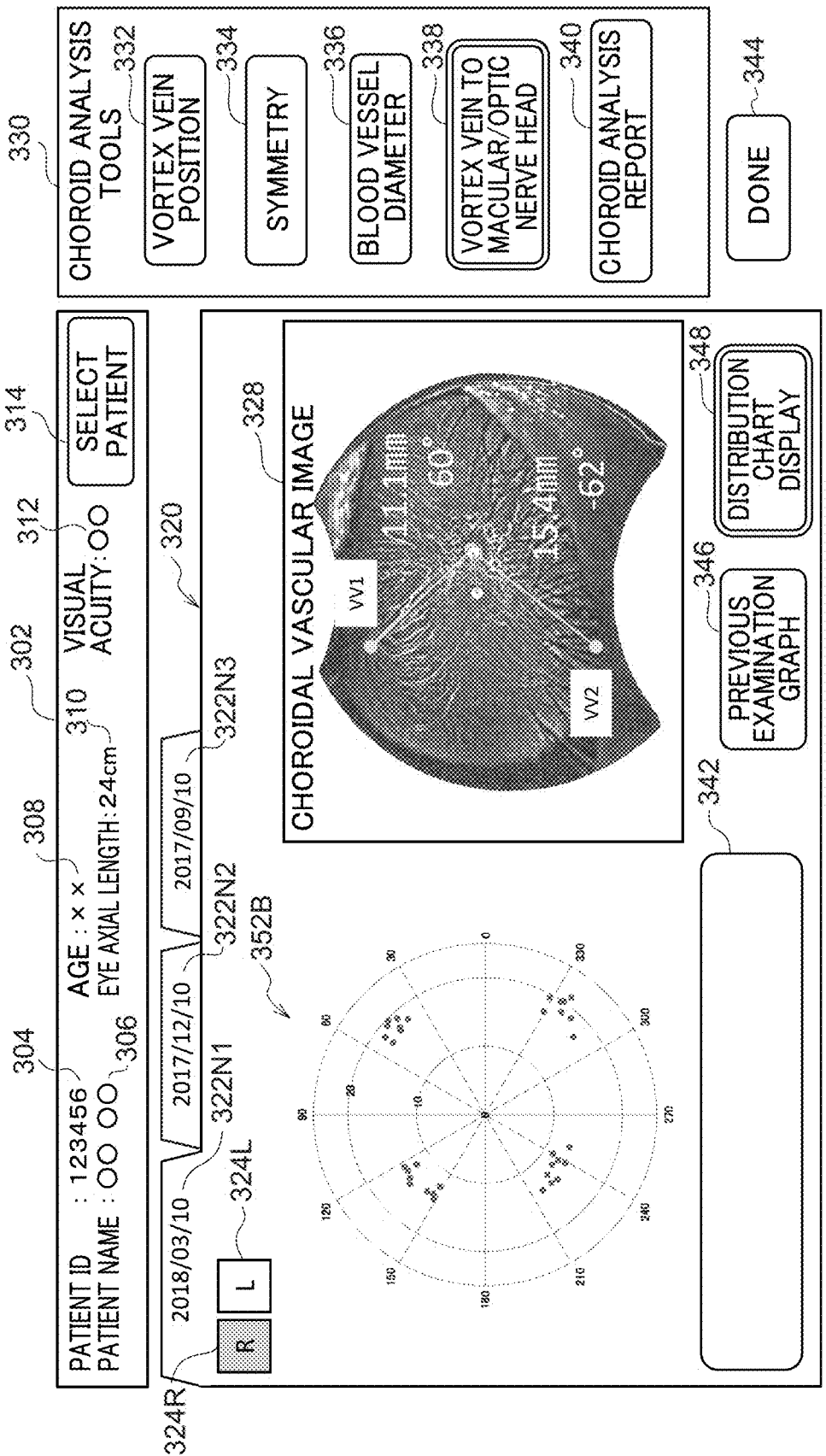
FIG. 15 is a diagram illustrating a display screen 300 on which a different distribution chart 352B is displayed when a distribution chart display icon 348 is clicked.

When the distribution chart display icon 348 is clicked in the display screen 300 of FIG. 12, the distribution chart 352A illustrated in FIG. 14 is displayed. In the distribution chart 352A, the VV positions are displayed according to the positional relationships with respect to an up/down direction axis and an ear side-nose side axis. The distribution chart is not limited to the distribution chart 352A illustrated in FIG. 14, and a distribution chart 352A as illustrated in FIG. 15 may be displayed in which VV positions are displayed according to the positional relationships with respect to the center of the fundus image at the center, and at angles with respect to a horizontal line from the center toward the right side of the fundus. Note that the content displayed in the choroidal vascular image display field 328 has not been changed between FIG. 14 and FIG. 15.

In the present exemplary embodiment as described above, the feature values related to the positional relationship between the vortex vein position and the macular or the optic nerve head ONH position (the VV quantitative values) are computed, and the VV feature values are displayed with the VV feature values (the VV angles and the VV distances) superimposed on the fundus images (the RG image and the choroidal vascular image).

The present exemplary embodiment enables the VV feature values (the VV angles and the VV distances) to be displayed. This enables fundus diagnosis support to an ophthalmologist to be provided by displaying the relationship between the positions of the macular and optic nerve head, which are characteristic structures of a fundus, and the VV positions as numerical values of distance and angle.

Next, description follows regarding various modified examples of the technology disclosed herein.

FIRST MODIFIED EXAMPLE

Although in the above exemplary embodiment the distances and angles were found between the position of the optic nerve head ONH and the positions of the VVs and superimposed on the fundus image, the technology disclosed herein is not limited thereto. One or other out of the distances or the angles between the optic nerve head ONH position and the VV positions may be superimposed on the fundus image. Similar applies to the position of the macular M and the positions of the VVs.

SECOND MODIFIED EXAMPLE

In the exemplary embodiments described above, the distances between the optic nerve head ONH position and the VV positions is a distance on a spherical surface, however the technology disclosed herein is not limited thereto, and straight line distances between the optic nerve head ONH position and the VV positions may be employed. Note that straight line distances may also be employed for the distances between the macular M position and the VV positions in the first modified example.

THIRD MODIFIED EXAMPLE

Although in the exemplary embodiment described above the management server 140 executes the image processing program illustrated in FIG. 5 in advance, the technology disclosed herein is not limited thereto. For example, the following configuration may be adopted. The image viewer 150 transmits a command to the management server 140 when the vortex vein to macular/nerve head icon 338 illustrated in FIG. 11 is clicked. In response thereto, the management server 140 then executes the image processing program of FIG. 5, and the image viewer 150 displays the display screen of FIG. 12.

FOURTH MODIFIED EXAMPLE

In the exemplary embodiment described above an example has been described in which a fundus image is acquired by the ophthalmic device 110 with an internal light illumination angle of about 200 degrees. However, the technology disclosed herein is not limited thereto, and the technology disclosed herein may be applied even when the fundus image has been imaged by an ophthalmic device with an internal illumination angle of 100 degrees or less, and may also be applied to a montage image obtained by combining plural fundus images.

FIFTH MODIFIED EXAMPLE

In the exemplary embodiment described above the fundus image is imaged by the ophthalmic device 110 equipped with an SLO imaging unit. However, the technology disclosed herein may be applied to a fundus image imaged using a fundus camera capable of imaging the choroidal blood vessels, and to images obtained by OCT angiography.

SIXTH MODIFIED EXAMPLE

In the exemplary embodiment described above, the management server 140 executes the image processing program. However the technology disclosed herein is not limited thereto. For example, the image processing program may be executed by the ophthalmic device 110 or the image viewer 150. In cases in which the ophthalmic device 110 executes the image processing program, the image processing program is stored in the memory 24. Moreover, in cases in which the image processing program is executed by the image viewer 150, the image processing program is stored in the memory 164 of the image viewer 150.

SEVENTH MODIFIED EXAMPLE

The exemplary embodiment described above describes an example of the ophthalmic system 100 equipped with the ophthalmic device 110, the eye axial length measuring device 120, the management server 140, and the image viewer 150; however the technology disclosed herein is not limited thereto. For example, as a first example, the eye axial length measuring device 120 may be omitted, and the ophthalmic device 110 may be configured so as to further include the functionality of the eye axial length measuring device 120. Moreover, as a second example, the ophthalmic device 110 may be configured so as to further include the functionality of one or both of the management server 140 and the image viewer 150. For example, the management server 140 may be omitted in cases in which the ophthalmic device 110 includes the functionality of the management server 140. In such cases, the image processing program is executed by the ophthalmic device 110 or the image viewer 150. Moreover, the image viewer 150 may be omitted in cases in which the ophthalmic device 110 includes the functionality of the image viewer 150. As a third example, the management server 140 may be omitted, and the image viewer 150 may be configured so as to execute the functionality of the management server 140.

EIGHTH MODIFIED EXAMPLE

In the exemplary embodiments described above, the R fundus image imaged with the R-light is employed as the first fundus image, however the IR fundus image imaged with the IR-light may be employed therefor. Namely, employing R-light or IR-light means that light is employed that travels as far as the choroid from out of plural layers of different structure covering the vitreous body of the eyeball and including the retina and the choroid at positions in sequence from the side closest to the vitreous body outward.

NINTH MODIFIED EXAMPLE

In the exemplary embodiments described above, the fundus images are obtained by imaging the fundus of the examined eye 12 at the same time with both G-light and R-light. However the technology disclosed herein is not limited thereto. For example, imaging of the fundus of the examined eye 12 may be performed at chronologically shifted times for the G-light and R-light. In such cases positional alignment is performed on the first fundus image (R fundus image) and the second fundus image (G fundus image).

OTHER MODIFIED EXAMPLES

The data processing described in the exemplary embodiment described above is merely an example thereof. Obviously, unnecessary steps may be omitted, new steps may be added, and the sequence of processing may be changed within a range not departing from the spirit thereof.

Moreover, although in the exemplary embodiment described above an example has been given of a case in which data processing is implemented by a software configuration utilizing a computer, the technology disclosed herein is not limited thereto. For example, instead of a software configuration utilizing a computer, the data processing may be executed solely by a hardware configuration of field programmable gate arrays (FPGAs) or application specific integrated circuits (ASICs). Alternatively, a portion of processing in the data processing may be executed by a software configuration, and the remaining processing may be executed by a hardware configuration.

What is claimed is:

1. An image processing method comprising:
analyzing a choroidal vascular image and detecting a vortex vein position; and
computing a feature value based on the vortex vein position and a particular position on a fundus.

2. The image processing method of claim 1, wherein the feature value is a positional relationship between the vortex vein position and the particular position.

3. The image processing method of claim 1, wherein the feature value is a distance between the vortex vein position and the particular position.

4. The image processing method of claim 3, further comprising generating a feature value superimposed fundus image in which either a line segment connecting the vortex vein position to the particular position, or a numerical value indicating the distance, is displayed so as to be superimposed on a fundus image.

5. The image processing method of claim 1, wherein the particular position is a position of a characteristic structure.

6. The image processing method of claim 1, wherein the particular position is specified by analysis of a fundus image.

7. The image processing method of claim 1, wherein the particular position is a position of an optic nerve head or a position of a macular.

8. The image processing method of claim 1, wherein:
the particular position includes a first particular position and a second particular position; and
the feature value is an angle defined by a first line segment connecting the vortex vein position to the first particular position, and a second line segment connecting the first particular position to the second particular position.

9. The image processing method of claim 8, wherein the feature value includes a distance between the vortex vein position and the first particular position.

10. The image processing method of claim 9, further comprising:
generating a feature value superimposed fundus image in which
the first line segment connecting the vortex vein position to the first particular position,
the second line segment connecting the first particular position to the second particular position, a numerical value indicating the distance between the vortex vein position and the first particular position, and a numerical value indicating the angle defined by the first line segment and the second line segment, are displayed superimposed on a fundus image.

11. The image processing method of claim 8, wherein the first particular position is an optic nerve head, and the second particular positon is a macular.

12. The image processing method of claim 1, wherein computing the feature value includes:

projecting each coordinate of a vortex vein and the particular position onto a surface of a virtual sphere, and computing a feature value indicating a positional relationship between a position of the vortex vein and the particular position on the surface of the virtual sphere.

13. The image processing method of claim 1, wherein detecting the vortex vein position includes estimating the vortex vein position based on a blood vessel running direction of a choroidal blood vessel.

14. The image processing method of claim 1, further comprising:

generating an image in which the feature value is displayed in a state of being superimposed on a fundus image.

15. The image processing method of claim 1, further comprising:

generating an image in which a line segment connecting the vortex vein position to the particular position is displayed in a state of being superimposed on a fundus image.

16. A non-transitory storage medium storing a program executable by a computer to perform an image processing method comprising:

analyzing a choroidal vascular image and detecting a vortex vein position; and computing a feature value based on the vortex vein position and a particular position on a fundus.

17. An image processing device comprising:

a memory that stores a program that causes a processor to execute an image processing method; and a processor that executes the program stored in the memory to perform operations comprising:

analyzing a choroidal vascular image and detecting a vortex vein position; and computing a feature value based on the vortex vein position and a particular position on a fundus.

* * * * *